US012805710B2

(12) United States Patent
Sørensen et al.

(10) Patent No.: US 12,805,710 B2
(45) Date of Patent: Nov. 24, 2026

(54) TIP PART FOR A VIDEOSCOPE AND A VIDEOSCOPE INCLUDING SAID TIP PART

(71) Applicant: AMBU A/S, Ballerup (DK)

(72) Inventors: Morten Sørensen, Ballerup (DK); Troels Nicolaj Qvist, Roskilde (DK)

(73) Assignee: AMBU A/S, Ballerup (DK)

( * ) Notice: Subject to any disclaimer, the term of this patent is extended or adjusted under 35 U.S.C. 154(b) by 137 days.

(21) Appl. No.: 18/972,371

(22) Filed: Dec. 6, 2024

(65) Prior Publication Data

US 2025/0098949 A1 Mar. 27, 2025

Related U.S. Application Data

(63) Continuation of application No. 16/818,141, filed on Mar. 13, 2020, now Pat. No. 12,185,922.

(30) Foreign Application Priority Data

Mar. 14, 2019 (EP) .................................... 19162924

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00048* (2013.01); *A61B 1/0055* (2013.01); *A61B 1/0676* (2013.01)

(58) Field of Classification Search
CPC ....... A61B 1/008; A61B 1/05; A61B 1/00048; A61B 1/0055; A61B 1/0676;
(Continued)

(56) References Cited

U.S. PATENT DOCUMENTS 5,609,561 A 3/1997 Uehara et al.
5,993,378 A 11/1999 Lemelson
(Continued)

FOREIGN PATENT DOCUMENTS

EP 3539449 A1 9/2019
EP 3708061 A1 9/2020
(Continued)

OTHER PUBLICATIONS

European Extended Search Report in related European Application No. 19162924, dated Sep. 11, 2019.
(Continued)

*Primary Examiner* — Michael J Carey
*Assistant Examiner* — Stephen Floyd London
(74) *Attorney, Agent, or Firm* — Faegre Drinker Biddle & Reath LLP

(57) ABSTRACT

A videoscope with a tip part including a camera assembly having an image sensor and a first light source and a first tolerance compensator having a pre-compensation condition and a post-compensation condition, wherein movement from the pre-compensation condition to the post-compensation condition adjusts a distance along the optical axis of the first light source between the first light source and the image sensor, and wherein in the post-compensation condition the first tolerance compensator maintains the distance between the first light source and the image sensor at least along the optical axis of the first light source.

17 Claims, 5 Drawing Sheets

(51) Int. Cl.
*A61B 1/005* (2006.01)
*A61B 1/06* (2006.01)

(58) Field of Classification Search
CPC ... A61B 1/00096; A61B 1/0011; A61B 1/051; A61B 1/0607; A61B 1/0684; A61B 1/07; A61B 1/00057; A61B 1/00071; A61B 1/012; A61B 1/04; A61B 1/06; A61B 1/00101; A61B 1/053; A61B 1/0627; G02B 23/243; G02B 23/2476; G02B 23/2484; H04N 23/56
See application file for complete search history.

(56) References Cited

U.S. PATENT DOCUMENTS 6,547,721 B1 4/2003 Higuma et al.
8,277,375 B2 10/2012 Danitz et al.
8,485,966 B2 7/2013 Robertson
9,125,582 B2 9/2015 Petersen
9,220,400 B2 12/2015 Petersen
9,320,419 B2 4/2016 Kirma et al.
9,622,649 B2 4/2017 Lin
9,814,374 B2 11/2017 Kirma et al.
9,854,962 B2 1/2018 Mcgrail et al.
10,321,804 B2 6/2019 Jacobsen et al.
10,406,309 B2 9/2019 Daher
10,478,054 B2 11/2019 Nave et al.
10,499,798 B2 12/2019 Kitano
11,974,723 B2 5/2024 Qvist et al.
12,185,922 B2 1/2025 Sørensen et al.
2004/0027459 A1 2/2004 Segawa et al.
2004/0064018 A1 4/2004 Dunki-Jacobs et al.
2007/0049800 A1 3/2007 Boulais
2007/0249907 A1* 10/2007 Boulais ................ A61B 1/0676 600/179
2008/0027276 A1* 1/2008 Rovegno ............ G02B 23/2461 600/109
2008/0091064 A1 4/2008 Laser
2008/0300457 A1* 12/2008 Hosaka .............. A61B 1/00096 600/110
2009/0185392 A1 7/2009 Krupa et al.
2011/0118549 A1* 5/2011 Han ......................... A61B 1/04 29/854
2012/0065469 A1 3/2012 Allyn et al.
2012/0323078 A1 12/2012 Kikumori et al.
2013/0172670 A1 7/2013 Levy et al.
2013/0175720 A1 7/2013 Otsuka et al.
2013/0265798 A1* 10/2013 Kudo ................... A61B 1/0655 362/574
2013/0274551 A1 10/2013 Kirma et al.
2014/0073853 A1 3/2014 Swisher et al.
2014/0081085 A1 3/2014 Takato et al.
2014/0148644 A1 5/2014 Levi et al.
2014/0210976 A1* 7/2014 Lin ...................... A61B 1/0684 348/68
2014/0213850 A1 7/2014 Levy et al.
2014/0296643 A1 10/2014 Levy et al.
2015/0005580 A1 1/2015 Petersen
2015/0346586 A1 12/2015 Lin
2016/0106306 A1 4/2016 Furuta
2016/0220107 A1 8/2016 Scott et al.
2016/0374544 A1 12/2016 Kirma et al.
2017/0245734 A1 8/2017 Kaneko
2017/0248734 A1 8/2017 Barfoot et al.
2017/0325663 A1 11/2017 Levy et al.
2018/0028053 A1 2/2018 Kirma et al.
2018/0055334 A1* 3/2018 Ando ................. A61B 1/00112
2018/0132707 A1 5/2018 Aoki et al.
2018/0242831 A1* 8/2018 Hosaka ................ A61B 1/0676
2018/0344140 A1 12/2018 Aizenfeld
2019/0029494 A1 1/2019 Araki
2019/0133640 A1 5/2019 Charvet et al.
2019/0223694 A1 7/2019 Lund et al.
2019/0246884 A1 8/2019 Lu et al.
2019/0254504 A1 8/2019 Ide
2019/0282070 A1 9/2019 Sørensen et al.
2019/0285471 A1 9/2019 Milo et al.
2019/0384013 A1 12/2019 Nakagawa
2020/0196434 A1* 6/2020 Kuo ....................... H04N 23/57
2020/0288953 A1 9/2020 Sorensen et al.
2020/0297193 A1* 9/2020 Takahashi .............. G02B 7/021
2020/0405137 A1 12/2020 Qvist et al.
2021/0127953 A1* 5/2021 Oyama .............. A61B 1/00096
2023/0130203 A1 4/2023 Hansen et al.
2024/0225431 A1 7/2024 Sørensen et al.

FOREIGN PATENT DOCUMENTS

JP 2004-248835 A 9/2004
JP 3764512 B2 4/2006
JP 2018-015250 A 2/2018
WO 2010/066790 A1 6/2010
WO 2014/106511 A1 7/2014
WO 2016/188543 A1 12/2016

OTHER PUBLICATIONS

International Preliminary Report on Patentability received for PCT Patent Application No. PCT/EP2019/056489, mailed on Sep. 24, 2020, 07 pages.
International Search Report and Written Opinion issued by the European Patent Office, dated May 21, 2019, for International Application No. PCT/EP2019/056489; 9 pages.
Office Action received for European Application No. 21204436.6, mailed on Feb. 13, 2024, 6 pages.
Search Report issued by the European Patent Office, dated Oct. 26, 2018, for related Application No. EP18161746; 5 pages.
Search Report received for EP Application No. 21204436.6, mailed on Mar. 30, 2022, 9 page.

* cited by examiner

TIP PART FOR A VIDEOSCOPE AND A VIDEOSCOPE INCLUDING SAID TIP PART

The present application is a continuation of U.S. patent application Ser. No. 16/818,141 filed Mar. 13, 2020, which claims priority from European Application No. 19162924.5, filed Mar. 14, 2019; the disclosures of said applications are incorporated by reference herein in their entireties.

TECHNICAL FIELD

The present disclosure relates to endoscopes, and more specifically to an articulated tip part for an endoscope.

BACKGROUND

Videoscopes have general features and may have features specific to the procedures from which they derive their name, including the length of the insertion tube, whether they comprise a working channel to collect samples, etc. Medical videoscopes comprise endoscopes, colonoscopes, ear-nose-throat scopes, duodenoscopes, and any other medical device having an image sensor configured to obtain images of views of a patient. The term "patient" herein includes humans and animals. Portable medical monitors can be communicatively coupled to the medical videoscopes to receive image data therefrom and present images corresponding to the image data on a display module of the monitor. An endoscope is a type of a videoscope.

Endoscopes are well known for visually inspecting inaccessible places such as body cavities. Typically, the endoscope comprises an elongated insertion tube with a handle at the proximal end, as seen from the operator, and visual inspection means, such as a built-in camera, at the distal end of the elongated insertion tube. This definition of the terms distal and proximal, i.e. proximal being the end closest to the operator and distal being the end remote from the operator, as used herein for endoscopes in general, is adhered to in the present specification. The term "endoscope" in the present context is a equivalent to videoscope and does also include laryngoscopes and endotracheal tubes provided with a camera for surveillance of correct positioning.

An endoscope, described in commonly owned U.S. Patent Application No. 2019/0223694, has an insertion tube with an internal working channel and a connector at the handle adapted for the attachment of a syringe. A recess is adapted to accommodate a cylindrical body of the syringe when the syringe is attached to the connector. The endoscope is adapted to perform bronchoalveolar lavage, a procedure for obtaining samples, through the working channel, of organic material from a lung segment of a patient.

As mentioned above, a videoscope can also comprise a endobronchial tube with an image sensor, as described in commonly owned U.S. Pat. Nos. 10,321,804 and 10,406,309. The endobronchial tube comprises a tube having a wall, a first inflatable cuff, a second lumen having an open distal end, a second inflatable cuff, a dedicated image sensor lumen in the wall, an image sensor, and an illumination source within the dedicated image sensor lumen at the distal end thereof. The endobronchial tube may include a dedicated cleaning nozzle arrangement embedded in the wall of the tube.

A videoscope can also comprise an endotracheal tube with an image sensor, as described in commonly owned U.S. Pat. No. 10,478,054. The endotracheal tube comprises a tube having a wall defining a ventilation lumen, an image sensor, and an illumination source within a dedicated image sensor lumen at the distal end of the endotracheal tube.

A videoscope can also comprise a video laryngoscope, as described in commonly owned U.S. Pat. No. 9,854,962. The video laryngoscope includes a housing including a display screen, a battery compartment, and a blade. The blade includes an open channel provided to guide insertion of an endotracheal tube. An image sensor is positioned at a distal end of the blade. The image sensor can be part of the blade or can be connected to the housing and introduced into a cavity of a disposable blade.

As the name indicates, videoscopes are used for seeing inside things, such as lungs or other human body cavities of a patient. Modern endoscopes are therefore typically equipped with a light source and a vision receptor including a vision sensor, such as a camera or an image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode or an optical fibre, may provide illumination.

Electrical wiring for the camera and other electronics, such as LED lighting accommodated in the tip part at the distal end, run along the inside of the elongated insertion tube from the handle to the tip part. Instead of using cameras, endoscopes may also be fibre-optic, in which case the optical fibres run along the inside of the elongated insertion tube to the tip part. For some applications, a working or suction channel may run along the inside of the insertion tube from the handle to the tip part, e.g. allowing liquid to be removed from the body cavity, allowing injection of fluid into the body cavity, or allowing for insertion of surgical instruments or the like, into the body cavity. The suction channel may be connected to a suction connector, typically positioned at a handle at the proximal end of the insertion tube. For other applications, the working or suction channel may be omitted.

In order to be able to maneuver the endoscope inside the body cavity, the distal end of the endoscope may comprise a bending section with increased flexibility, e.g. an articulated tip part allowing the operator to bend this section. Typically, this is done by tensioning or slacking steering wires also running along the inside of the elongated insertion tube from the articulated tip part to a control mechanism of the handle.

For an operator to be able to move the endoscope into the correct position and to reliably inspect the body cavity, it is therefore desirable that good illumination is provided so that high quality imaging can be produced.

A general desire in the field of endoscopy is to electrically insulate the insertion tube, and thus especially the tip part, from the outside, so as to mitigate the risk of an insulation breakdown and a resulting excessive leakage current.

Another general desire in the field of endoscopy is to provide a tip part which is liquid-sealed, so as to mitigate liquid ingress into the tip part, and specifically onto any electrical or optical components of the tip part.

A general desire in the field of endoscopy is to miniaturise the insertion tube of the endoscope, and thus the tip part, as this may open up new fields of application which requires an insertion tube with a smaller outer circumference than for instance bronchoscopy. Alternatively, miniaturising may allow the provision of a larger working channel diameter, maintaining the same outer diameter.

SUMMARY

On this background, it may be seen as an object of the present disclosure to provide an improved tip part for an endoscope, and an endoscope including said tip part, alleviating or meeting at least some of the above-mentioned desires.

One or more of these objects may be met by aspects of the present disclosure as described in the following.

A first aspect of this disclosure relates to a tip part for an endoscope, the tip part having a pre-compensation condition and a post-compensation condition, and comprising: a camera assembly having an image sensor and a first light source configured for emitting light along an optical axis thereof to provide illumination of an object to be visualised by the image sensor; and a first tolerance compensating member, or first tolerance compensator, being configured to, in the pre-compensation condition, allow adjustment of the distance between the first light source and the image sensor along the optical axis of the first light source and the first tolerance compensating member being configured to, in the post-compensation condition, maintain the distance between the first light source and the image sensor at least along the optical axis of the first light source.

In order to achieve a more consistent optical performance of the light source and image sensor, it is desired that the relative distance between these components can be controlled precisely so that they will abut their intended surfaces of for instance a window of the tip part when fully assembled. However, when manufacturing and assembling the components of the tip part for an endoscope, a relatively long tolerance chain often affects the relative positioning of the image sensor and light source, for instance the soldering height on a printed circuit board or manufacturing and assembly variations. There is a risk that this adversely affect the optical performance of the tip part, such as non-optimal illumination provided by the light source and the quality of the image produced by the image sensor. By providing such a tolerance compensating member and by decoupling the movement of the light source and image sensor, the distance between the light source and the image sensor may be adjusted after the camera assembly has been assembled and thus break the assembly tolerance chain. A tip part of this type provides the advantage of reducing or even eliminating said risk to provide a more consistent optical performance of the camera assembly.

The first tolerance compensating member may be configured to allow an operator to adjust the distance between the first light source and the image sensor in the pre-compensation condition. The first tolerance compensating member may be configured to move axially independently of the image sensor.

The tip part may further comprise a second light source configured for emitting light along an optical axis to provide illumination for the image sensor. The second light source may be provided in the same way as the first light source. The second light source may be provided on an opposite side of the image sensor.

The tip part may further comprise a second tolerance compensating member configured to allow adjustment of the distance between the second light source and the image sensor along the optical axis of the second light source. The second tolerance compensating member may be provided in the same way as the first tolerance compensating member and may be provided on an opposite side of the image sensor.

The camera assembly may allow an operator to inspect a body cavity, when the tip part is inserted into the body cavity. The camera assembly may further comprise one, some, or all elements selected from the group consisting of: at least one lens configured to alter light received by the image sensor, a holder for supporting the parts of the camera assembly, at least one light source configured to provide illumination for the image sensor, a printed circuit board, at least one signal cable for carrying an image signal from the camera assembly to the operator, and a battery for powering the camera assembly or a power cable for supplying the camera assembly with electricity from a power source connected to the operating handle. The signal cable may be configured for transmitting an image signal to an operating handle of the endoscope or an output for a monitor. The power cable may be configured to supply power to the printed circuit board from a power source.

The printed circuit board may form electrical connections to the remaining electrical components of the camera assembly, such as the light source(s), the image sensor, the signal cable(s), and/or power cable(s). The printed circuit board may be configured to process a signal from the image sensor. The printed circuit board may be a flexible printed circuit board configured to be folded, potentially around the holder of the camera assembly.

The light source(s) may be positioned at the distal portion of the camera assembly potentially so that light emitted from the light source(s) is directed distally. At least one or all of the light source(s) may be light emitting diode(s) or light fibre(s). The light source(s) may be configured for providing illumination for the image sensor of the camera assembly. The number of light sources may be at least two or at the most two or exactly two.

The optical axis may be a longitudinal optical axis. The potentially longitudinal optical axis may extend from a proximal end of the tip part to a distal end of the tip part.

Additionally or alternatively, the tip part may comprise an exterior housing part. The exterior housing part may provide structural integrity to the tip part and may aid in liquid-sealing electronic components of the camera assembly. The exterior housing part may be positioned at a distal end of the tip part. The exterior housing part may have a distal end, potentially forming the distal end of the tip part. The exterior housing may have a proximal end and a distal end.

The exterior housing part may be cup-shaped. The exterior housing part may be substantially shaped as a closed cylinder open in the proximal end by the proximal opening and closed in the distal end by a distal wall. The distal wall may comprise a window, which may allow light to propagate there-through to the image sensor of the camera assembly, or a distal opening, potentially adjacent and sealed to the camera assembly, so that a portion of light passing through the opening is received by an image sensor of the camera assembly.

The exterior housing part may be manufactured by an injection moulding process. The exterior housing part may be made of a polymer material. The exterior housing part may be two-component moulded, so as to be a single part comprising two different materials, often polymer materials. A first material may be transparent, and a second material may be translucent, opaque, and/or coloured. This may provide the advantage that the exterior housing part can be manufactured as one sealed assembled component without an extra process step, such as adhesion or welding, with advantageous properties, such as forming providing the first, transparent material in the distal wall of the exterior housing part to form one or more window in front of the image sensor and/or lens(es) to allow the image sensor to produce an image while still having a sealed housing surrounding the camera assembly.

Additionally or alternatively, the tip part may comprise a bending section. The bending section may allow the tip part to be articulated and bend relative to non-articulated parts of the tip part, for instance the flexible tube or the exterior housing part. The bending section may allow an operator to manipulate the tip part, potentially by operating a control element of an operating handle, while inserted into a body cavity of a patient.

The interior housing part may be attached to the bending section by adhesion between the attachment surface and the distal segment of the bending section. The bending section may be integrally formed, potentially in one piece.

At least one hinge member may interconnect adjacent segments of the bending section with each other, e.g. the proximal end segment with an adjacent intermediate segment, the distal end segment with an adjacent intermediate segment, and two intermediate segments with each other.

Additionally or alternatively, each pair of adjacent segments may be interconnected by at least one, two, or three hinge members. The hinge member(s) may be bridging a gap between adjacent segments. The hinge member may allow adjacent segments to pivot relative to each other to allow the bending section to bend. Each hinge member may be formed as a film hinge, e.g. a solid connection between adjacent segments which is relatively slim compared to the segment diameter.

Each segment of the bending section may comprise a similar, potentially substantially equal, outer, surface, potentially circumferentially extending around a central, proximal-distal axis of the bending section or tip part. The segments may be substantially cylindrically and/or disc-shaped. The outer surface of each segment may form part of an outer circumferentially extending side wall, which may extend around a central axis, potentially a proximal-distal axis, of the tip part. Each segment may be provided so that the bending section has a uniform outer contour. The optical axis may extend in parallel to the proximal-distal direction.

Additionally or alternatively, the hingedly interconnected segments may comprise or consist essentially of polypropylene (PP), polyethylene (PE), and/or polyoxymethylene (POM). The bending section may be integrally formed, potentially in one piece including segments including a distal end segment, a proximal end segment, the intermediate segments between the distal end and proximal end segments, and the hinges connecting adjacent of the segments.

The tip part may comprise one or more working passages. Each working passage may be configured for accommodating a working channel tube providing a working channel. The attachment surface may in this case extend partially around the circumference of the tip part and the working channel tube may form the remaining extent so that the attachment surface and the working channel tube together form a surface extending around the entire circumference, said surface being configured for connection with the bending section. One of the working channels may be a suction channel for providing a suction at the distal end of the tip part. The suction channel may be connected to a suction connector, potentially at a handle at the proximal end of the insertion tube. One of the working channels may allow insertion of surgical instruments there through to the distal end of the tip part. One of the working channels may be a flushing channel for injecting a fluid out from the distal end of the tip part. A distal section of the working passage may form part of the exterior housing part and may be a separate open-ended cylinder positioned adjacent to the interior space in which the camera assembly is positioned. Alternatively, the working passage may be omitted to minimize the size of the tip part.

The segments may comprise at least one cable passage for accommodating at least one cable, e.g. the signal cable for carrying an image signal and/or the power cable for carrying electricity. The cable passage may comprise a through hole in each of the segments, potentially so as to form a cable passage, that may be extending from the distal end segment through the intermediate segment(s) to the proximal end segment. The cable passage may be positioned adjacent to a centre of the segments. The signal and/or the power cable may be positioned in the cable passage. The cable passage may be different from the working passage.

The tip part may comprise at least one, preferably two, steering wire(s). Each steering wire may further be positioned in a steering wire passage of the tip part. Each steering wire passage may be formed by a number of through holes provided in the segments of the tip part. Each steering wire passage may be different from the cable passage and/or the working passage. An end of the steering wire may be secured in the tip part, and another end of the steering wire may be connected to a control element, potentially a control lever of the control element. Thus by manipulating the control element or lever the steering wire may be tensioned on one side of the plane of the hinge members, and slacked on the other, thus allowing the bending section to bend in a desired direction.

Additionally or alternatively, the tip part may form part of an insertion tube for an endoscope, the insertion tube comprising a flexible tube. The flexible tube may be attached to the proximal end segment. The flexible tube may comprise an interior space defined by an outer circumferentially extending side wall. The outer circumferentially extending side wall may comprise an inner surface and an outer surface. The flexible tube may comprise a distal end, which may be connected to the proximal end segment of the bending section. The flexible tube may comprise a proximal end configured for connection with remaining parts of the endoscope, for instance an operating handle of the endoscope. The flexible tube may be integrally provided in one piece. The flexible tube may comprise or consist essentially of a polymer material, potentially supported by a metal braiding. The flexible tube may surround or enclose the cable passage and/or the working passage and/or the steering wire(s).

Additionally or alternatively, the tip part may comprise a tubular sleeve. The tubular sleeve may cover at least the intermediate segments and may seal any gaps between adjacent segments. The tubular sleeve may also be known as a bending cover. The tubular sleeve may seal the connection between the bending section and an adjacent element of the tip part, for instance the flexible tube and/or the exterior housing part. The tubular sleeve may provide the tip part and/or the flexible tube with an outer surface configured for insertion into a body cavity, for instance a substantially smooth outer surface. The wall thickness of the tubular sleeve may be less than 0.3, 0.25, 0.2, 0.15, 0.1, 0.09, 0.08, or 0.07 mm. The tubular sleeve may be made of a polymeric material which may be opaque, translucent, or transparent, for instance polyurethane elastomers, such as the polymer traded under the trademark Pellethane® as of February 2019.

The flexible tube, the exterior housing part, the interior housing part, the tubular sleeve, and the bending section may be provided as separate prefabricated components.

In some embodiments, the tip part may be a single-use or disposable tip part, potentially for a single-use or disposable endoscope, and may not be intended for cleaning and/or reusing.

In this specification, the term "exterior", such as in "exterior housing part", may be understood as a portion configured for facing a body cavity when the tip part is inserted into a body and thus provide a sealing function, and additionally the term "interior" may be understood as a portion intended to be surrounded by another component or components of the tip part. For instance, an interior housing part may be surrounded by exterior housing part and the bending section.

Additionally or alternatively, the first tolerance compensating member may be configured to, in the pre-compensation condition, move the first light source along the optical axis of the first light source relative to the image sensor.

This may provide the advantage of a particularly simple way of adjusting the distance between the first light source and the image sensor, since the image sensor may be positioned correctly first and then the first light source can be adjusted accordingly by the first tolerance compensating member.

The tolerance compensating member may be configured to move the light source along the optical axis thereof, potentially until a light emitting surface of the light source, abuts or contacts an interior surface of the exterior housing part, potentially a light guide surface of the exterior housing part.

The tolerance compensating member may comprise an arm or a spring configured for pushing the light source in the optical axis. The operator may adjust the distance between the first light source and the image sensor by pushing a proximal end of the tolerance compensating member.

In this disclosure, an optical axis may be defined as a line along which there is some degree of rotational symmetry in an optical system such as a lens or light source.

Additionally or alternatively, the first tolerance compensating member may comprise a seat configured for guiding the adjustment of the distance between the first light source and the image sensor along the optical axis of the first light source.

This may provide the advantage of robustly guiding the light source within the exterior housing part and ensuring that the light source can be consistently moved to the desired location.

The seat may comprise a radial guide surface configured for preventing radial movement of the first light source during adjustment of the distance between the first light source and the image sensor. The seat may form part of an arm of the tolerance compensating member.

Additionally or alternatively, the first light source may be fixed to the first tolerance compensating member, potentially by an adhesive.

By fixating the light source, may provide the advantage that it is ensured that the light source follows the movements of the tolerance compensating member and therefore the adjustment of the light source may be more consistent.

The light source may be fixed by adhering the light source to the tolerance compensating member.

Additionally or alternatively, the tip part further comprises a printed circuit board being electrically connected to both the image sensor and the first light source.

This may provide the advantage of only having to electrically connect the first light source and the image sensor to the same printed circuit board.

The first light source and the image sensor may be electrically connected to the printed circuit board by soldering. The first light source and the image sensor may further be fixed to the same printed circuit board. The first light source may be a light emitting diode, and the image sensor and the first light source may be soldered onto the same printed circuit board of the tip part.

Additionally or alternatively, the tip part may further comprise: an exterior housing part including a circumferentially extending side wall with a proximal opening, the circumferentially extending side wall defining an interior space with an air volume; and an interior housing part including a circumferentially extending closure surface and the first tolerance compensating member, the interior housing part being positioned in the proximal opening of the exterior housing part, the tolerance compensating member and the interior housing part being integrally formed in one piece; wherein the camera assembly includes a distal portion and is positioned in the interior space so that the air volume envelops at least the distal portion of the camera assembly, and wherein the exterior housing part and interior housing part are formed as separate prefabricated components, and wherein the closure surface is configured for closing the proximal opening of the exterior housing so as to liquid-seal the air volume in tip part and fix the first light source relative to the image sensor.

By providing a tip part in this way, a number of advantages may be achieved. Firstly, the air volume can be liquid-sealed by adhesive with reduced risk of the adhesive flowing onto optical components of the tip part, such as lenses, light sources, light guides etc., thereby altering the optical properties of the tip part. This may provide the advantage that troubleshooting, reparability, or reusability of the tip part is improved. This may also provide a tip part which can be disassembled into components to be recycled.

Secondly, an assembled exterior housing part, interior housing part, and camera assembly can be tested for liquid tightness and electrical insulation prior to being further assembled, such as attached to a bending section, thus enabling faulty tip parts to be identified and corrected early in the assembly process thereby providing an increased assembly quality.

The closure surface may close the proximal opening to seal the air volume by itself, such as by forming a plug in the proximal opening, or by aid of another component, such as a hardened adhesive sealing to the closure surface and an interior surface of the exterior housing part.

Additionally or alternatively, the interior housing part may comprise a circumferentially extending attachment surface, wherein, when the interior housing part is positioned in the proximal opening of the exterior housing part, the attachment surface extends proximally from the proximal opening and is configured for attaching the interior housing part to another element, such as a distal end segment of a bending section, of the tip part.

The tip part may have an assembled position, wherein the closure surface may close the proximal opening so as to liquid-seal the air volume in the tip part in the assembled position, potentially by an adhesive, and/or the attachment surface may attach the interior housing part to another element of the tip part, potentially by an adhesive, in the assembled position.

By integrating the attachment surface into the interior housing part, a smaller outer circumference of the tip part may be obtained as the exterior housing part, which typically defines the lower bound of the outer circumference of the tip part, no longer forms the connection to other further elements of the tip part, such as a bending section. Thus by offloading this function to the interior housing part, the exterior housing part may be made with a smaller outer circumference.

Thus by providing a tip part in this way may provide the combined advantage of a liquid tight and miniaturised tip part with a robust attachment interface to remaining parts of the tip part.

The attachment surface may additionally be configured to allow an operator to insert and/or manipulate the interior housing part into the exterior housing part by hand.

Additionally or alternatively, the attachment surface may comprise one or more cut-outs configured for accommodating hardened adhesive to improve the mechanical connection between the attachment surface and the other element of the tip part. This may provide the advantage of improving an mechanical connection to the other element of the tip part, such as a distal end segment of a bending section.

The number of cut-outs may be at least one, at least two, or at least three. Each cut-out may be formed as a groove, a recess, or a hole. Each cut-out may extend circumferentially. Each cut-out may be configured for improving an mechanical connection to the other element of the tip part. The cut-outs could alternatively be formed as ridges or protrusions.

Additionally or alternatively, the tip part may further comprise a bending section including a number of hingedly interconnected segments including a distal end segment, a proximal end segment, and a plurality of intermediate segments positioned between the proximal end segment and the distal end segment, wherein the attachment surface of the interior housing part is attached to the distal end segment. By providing an attachment surface in this way, may provide the advantage that a strong connection between the interior housing part and the bending section can be formed.

The attachment surface may form part of a projection extending axially in a proximal direction from the proximal opening of the exterior housing part, so that the attachment surface overlaps with the distal end segment of the bending section when attached thereto. This may provide the advantage that a correct rotation of the bending section relative to the interior and exterior housing parts may be ensured. The distal end segment may comprise cut-outs to improve the mechanical connection between the distal end segment and the attachment surface.

Additionally or alternatively, a gap may be formed between the closure surface and an interior surface of the exterior housing part in the pre-compensation condition and when the interior housing part is positioned in the proximal opening of the exterior housing part, the gap being filled with a hardened adhesive in the post-compensation condition so as to liquid-seal the air volume and fix the first light source relative to the image sensor.

By adequately choosing a suitable gap size and adhesive viscosity, may provide the advantage that the adhesive may be drawn into the gap by a capillary effect ensuring that both the interior surface and the closure surface is sufficiently wetted along the entire circumference of the gap by the adhesive. This provides a strong structural connection and great sealing properties between the interior and exterior housing part. Furthermore, the adhesive, upon injection into the gap, may provide a centering force so that the thickness of the adhesive is substantially uniform around the circumference of the proximal opening.

The gap may be at least 5, 10, 15, or 20 micrometres prior to injection of adhesive. The gap may be at most 100, 90, 80, 70, 60, 55, or 50 micrometres. The gap may be in the range of 5-100, 10-90, 15-70, or 20-50 micrometres. A gap of this size has been found to provide a good capillary effect for distribution of the adhesive in the gap wherein narrower ranges provides a better effect.

Additionally or alternatively, the adhesive may be an ultraviolet curable adhesive as these may be cured on demand. The viscosity of adhesive may be in the range of 200-5000 cP, preferably about 1000 cP, as too low viscosity may cause the adhesive to flow too far into the gap and potentially onto electrical or optical components of the tip part and too high viscosity may prevent the adhesive from flowing into the gap.

Additionally or alternatively, the interior housing part may comprise a cavity configured for accommodating and aligning a guide portion of the camera assembly at the proximal end thereof. This may provide the advantage of ensuring that the proximal end of the camera assembly is aligned in the interior space, so that the image sensor is directed consistently.

The guide portion may form part of a holder of the camera assembly.

Additionally or alternatively, the interior housing part may comprise a hole configured for allowing a cable tube accommodating a plurality of cables electrically connected to the camera assembly to be inserted there through.

This may provide the advantage that in order to provide a liquid-sealed tip part while still allowing power and signals to flow to and from the camera assembly only a well-defined interface between the cable tube and the interior housing part has to be sealed.

The cable tube may be positioned in the cable passage of the bending section. The plurality of cables may be electrically connected to the light source(s), the printed circuit board, and the image sensor.

Additionally or alternatively, a gap may be formed at an overlap between the closure surface and an interior surface of the exterior housing, the overlap having a length of at least 0.5, 0.75, 1.0, or 1.1 mm in an axial direction of the tip part.

It has been found that a tip part of this kind allows a sufficiently strong and sealing connection between the closure surface and the interior surface of the exterior housing part.

Additionally or alternatively, an endoscope may comprise a tip part according to the first aspect of this disclosure.

The term "endoscope" may be defined as a device suitable for examination of natural and/or artificial body openings, e.g. for exploration of a lung cavity. Additionally, or alternatively, the term "endoscope" may be defined as a medical device, and may also cover laryngoscopes and endotracheal tubes provided with a camera for surveillance of correct positioning.

Additionally or alternatively, a system for visually inspecting inaccessible places such as human body cavities, may comprise:

- an endoscope with a tip part according to the first aspect of this disclosure, and a monitor, wherein the endoscope is connectable to the monitor, and the monitor allow an operator to view an image captured by the camera assembly of the endoscope.

In this disclosure, the proximal-distal axis may be defined as a central axis of the tip part from the proximal end to the distal end, for instance when the tip part is substantially cylindrically shaped, the proximal-distal axis may follow the centre line of this cylindrical shape. The proximal-distal axis may follow the shape of the tip part, so that if the bending section of the tip part is bent, then the proximal-distal axis follows the bending shape of the tip part.

A second aspect of this disclosure relates to a method for preparing a tip part for an endoscope, comprising the steps of: providing a tip part according to the first aspect of this disclosure, positioning a surface of the camera assembly, potentially a light receival surface of the camera assembly or a lens surface of the image sensor, in contact with a camera stop surface of another part, such as an exterior housing part or an assembly fixture, adjusting the first tolerance compensating member so that the first light source is moved in contact with a second stop surface of the other part, such as the exterior housing part or the assembly fixture, along the optical axis of the first light source, and fixing the first light source in relation to the image sensor, potentially by an adhesive.

When manufacturing and assembling a tip part for an endoscope, a long tolerance chain often affects the relative positioning of the image sensor and light source, for instance the soldering height on a printed circuit board or manufacturing and assembly variations. There is a risk that this adversely affect the optical performance of the tip part, such as non-optimal illumination provided by the light source and the quality of the image produced by the image sensor. By providing such a tolerance compensating member and by decoupling the movement of the light source and image sensor, the distance between the light source and the image sensor may be adjusted after the camera assembly has been assembled and thus break the assembly tolerance chain. A method of this type provides the advantage of reducing or even eliminating said risk to provide a more consistent optical performance of the camera assembly.

Additionally or alternatively, the step of positioning the camera assembly may comprise positioning the camera assembly, potentially a light receival surface of the camera assembly or a lens surface of the image sensor, in contact with a camera stop surface of assembly fixture. Further the second stop surface may form part of the assembly fixture. The method may further comprise a subsequent step of positioning the combined camera assembly and first tolerance compensating member in the exterior housing, and thereafter potentially fixing the first tolerance compensating member to the exterior housing.

Additionally or alternatively, the step of positioning the camera assembly may comprise positioning the camera assembly, potentially a light receival surface of the camera assembly or a lens surface of the image sensor, in contact with a camera stop surface of the exterior housing part. Further the second stop surface may form part of the exterior housing part. The first light source may be fixed to the first tolerance compensating member and the method may further comprise a step of fixing the tolerance compensating member to the exterior housing and thereby fixing the first light source in relation to the image sensor.

A person skilled in the art will appreciate that any one or more of the above aspects of this disclosure and embodiments thereof may be combined with any one or more of the other aspects of this disclosure and embodiments thereof.

BRIEF DESCRIPTION OF DRAWINGS

The aspects of this disclosure will now be described in greater detail based on non-limiting exemplary embodiments and with reference to the drawings, on which.

Figure 1A:
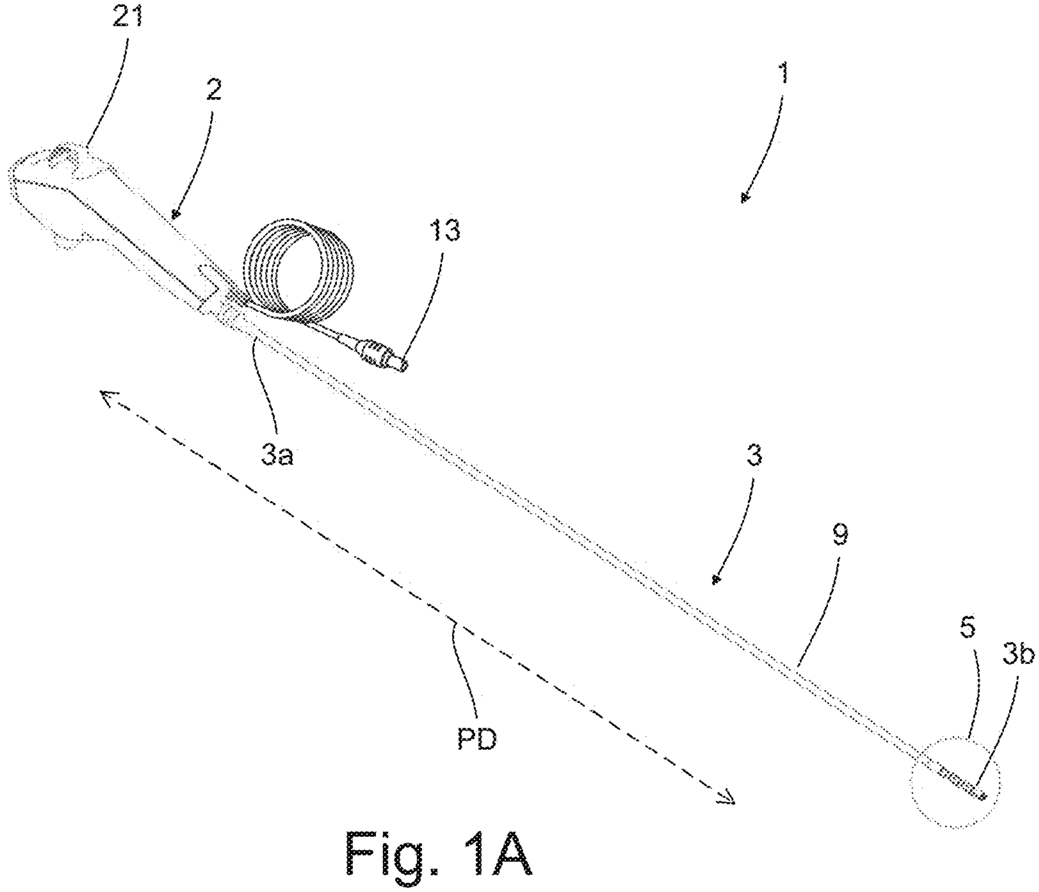
FIG. 1A shows a perspective view of an endoscope in which a tip part according to the present disclosure is implemented.

Referring first to FIG. 1A, an endoscope 1 is shown. The endoscope is disposable, and not intended to be cleaned and reused. The endoscope 1 comprises an elongated insertion tube 3. The insertion tube 3 is suitable for insertion into a lung of a body through a mouth. The body can be an artificial or natural body, for instance a human or animal body. At the proximal end 3*a* of the insertion tube 3 an operating handle 2 is arranged. The operating handle 2 has a control lever 21 for manoeuvring an articulated tip part 5 at the distal end 3*b* of the insertion tube 3 by means of a steering wire 31*a* running through a flexible tube 9. A camera assembly 8 is positioned in the tip part 5 and is configured to transmit an image signal through a monitor cable 13 of the endoscope 1 to a monitor 11.

Figure 1B:
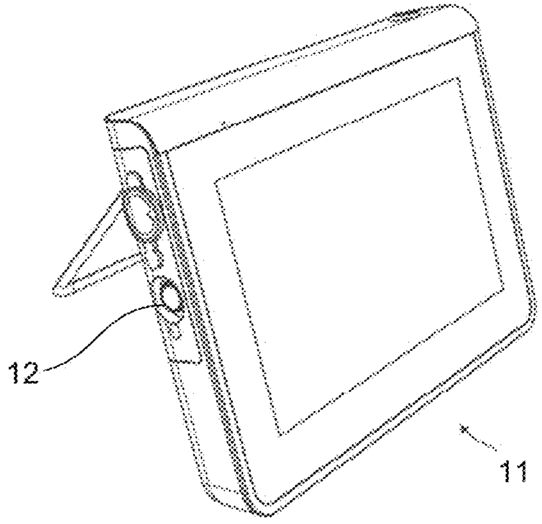
FIG. 1B shows a perspective view of a monitor to which the endoscope of FIG. 1A is connectable.

In FIG. 1B, a monitor 11 is shown. The monitor 11 allows an operator to view an image captured by the camera assembly 8 of the endoscope 1. The monitor 11 comprises a cable socket 12 to which a monitor cable 13 of the endoscope 1 can be connected to establish a signal communication between the camera assembly 8 of the endoscope 1 and the monitor 11.

Figure 2A:
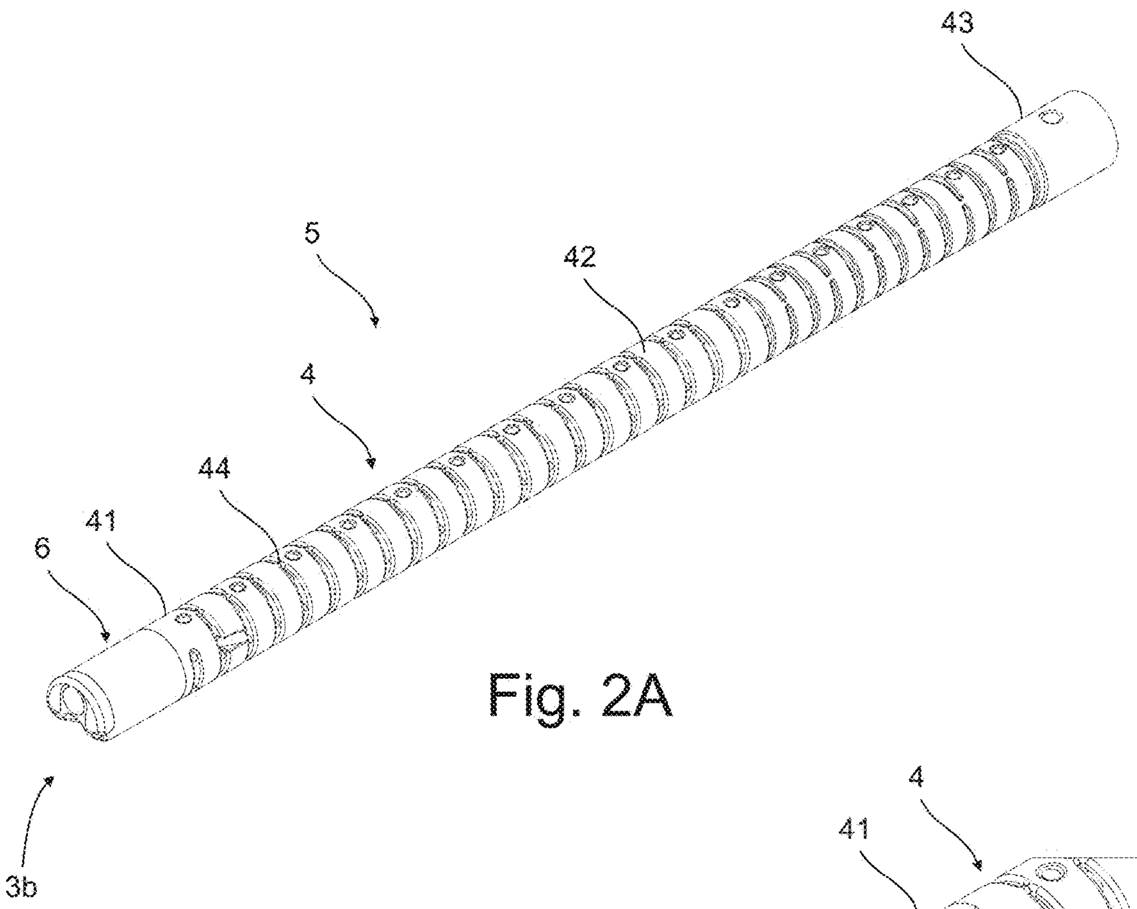
FIG. 2A shows a perspective view of an embodiment of a tip part according to the present disclosure in which a flexible tube is omitted.

Turning to FIG. 2A, the distal end 3*b* of the insertion tube 3 is shown and more specifically the articulated tip part 5. The tip part 5 comprises a bending section 4, and an exterior housing part 6. The bending section 4 comprises a number of hingedly connected segments including a proximal end segment 43, a distal end segment 41, and a plurality of intermediate segments 42 positioned between the proximal end segment 43 and the distal end segment 41. In the present embodiment, the number of intermediate segments 42 is about 32, but may in principle be less or even greater. Three hinge members 44 of the living hinge type interconnects each pair of adjacent segments. The hinge members 44 bridge a gap between adjacent segments. The bending section 4 allows the tip part 5 to bend relative to the flexible tube (omitted in this figure), so as to allow an operator to manipulate the tip part 5 while inserted into a body cavity. The bending section 4 and each hingedly interconnected segment 41, 42, 43 consist essentially of the same material and are integrally formed in one piece. The material is polyoxymethylene (POM) but may be any suitable material, such as polyethylene (PE) or polypropylene (PP). Typically, a tubular sleeve 8 for providing a smooth outer surface wraps around the bending section 4 but the tubular sleeve 8 is omitted in the figure for visualisation purposes. The tip part 5 further comprises a working passage 33 connected with a working tube 34 (shown foreshortened in length for visualisation purposes) to provide a working channel. The attachment surface 72 extends partially around the circumference of the tip part 5 and the working channel tube 34 may form the remaining extent so that the attachment surface 72 and the working channel tube 34 together form a surface extending around the entire circumference as best seen in FIG. 5C.

Figure 2B:
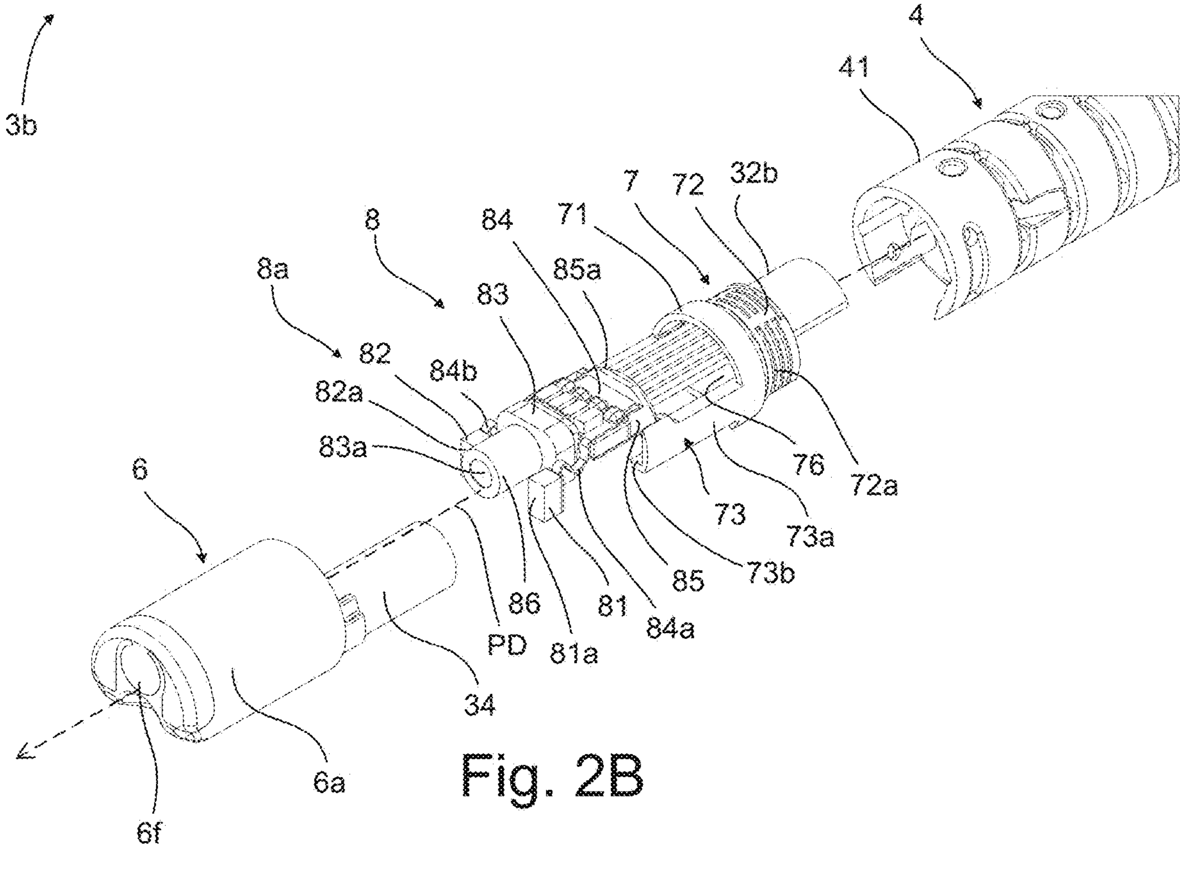
FIG. 2B shows an exploded perspective view of the tip part of FIG. 2A.
Figure 3A:
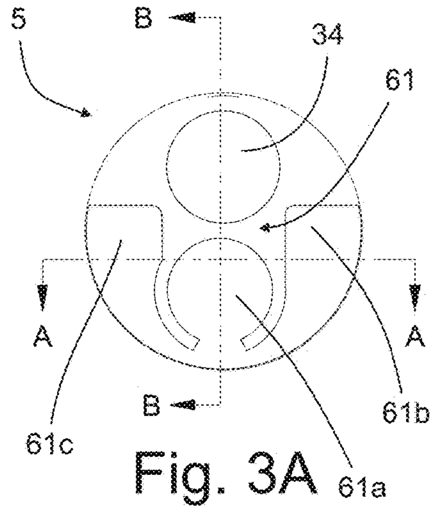
FIG. 3A shows a front view of the tip part of FIG. 2B with cross-sectional line A-A and B-B shown.
Figure 3C:
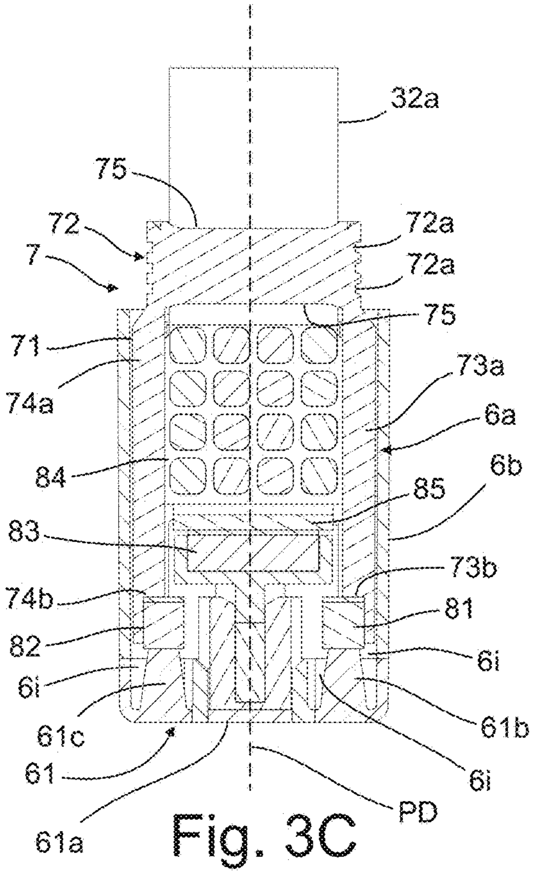
FIG. 3C shows a cross-sectional view of the tip part of FIG. 3A along the cross-section line A-A, in which the tip part is assembled.
Figure 3B:
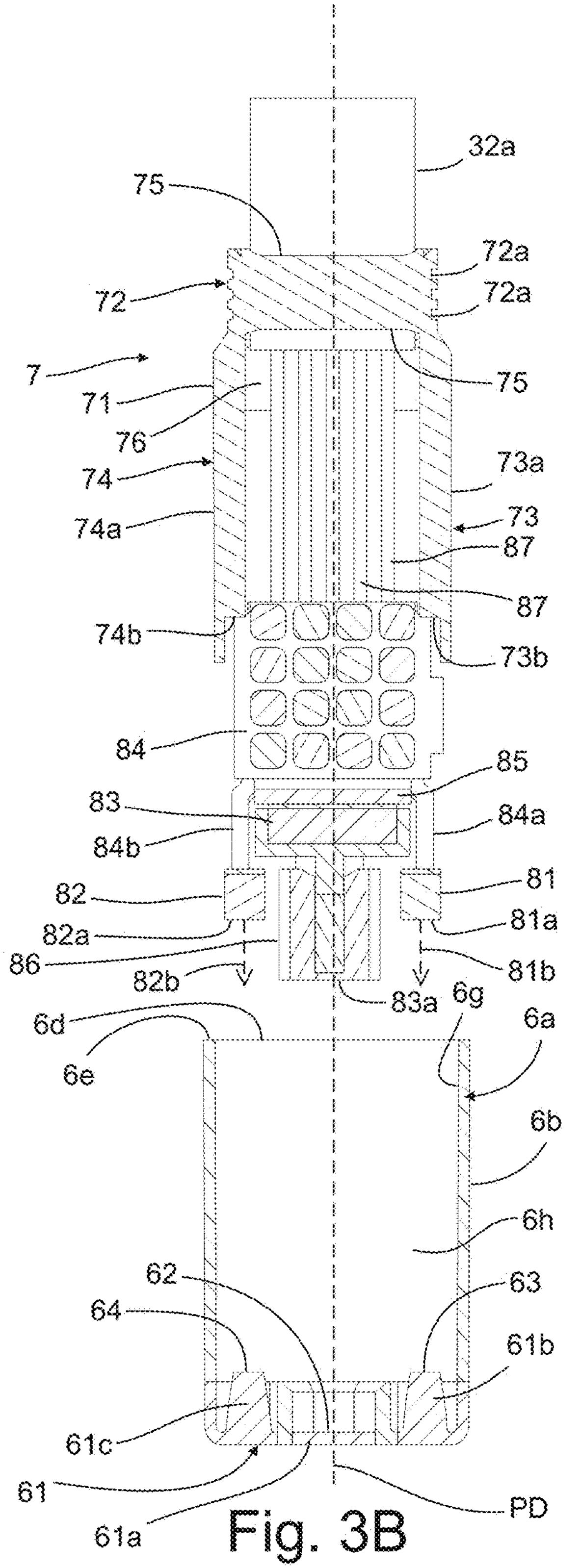
FIG. 3B shows a cross-sectional view of the exploded tip part of FIG. 3A along the cross-section line A-A.
Figure 4A:
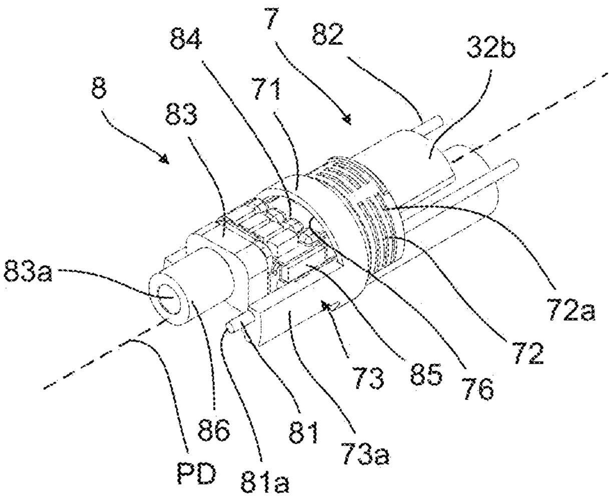
FIG. 4A shows a perspective view of another embodiment of a tip part according to the present disclosure in which an exterior housing part and a flexible tube are omitted, and in which a cable tube, cables, and light fibers are shown foreshortened.
Figure 4B:
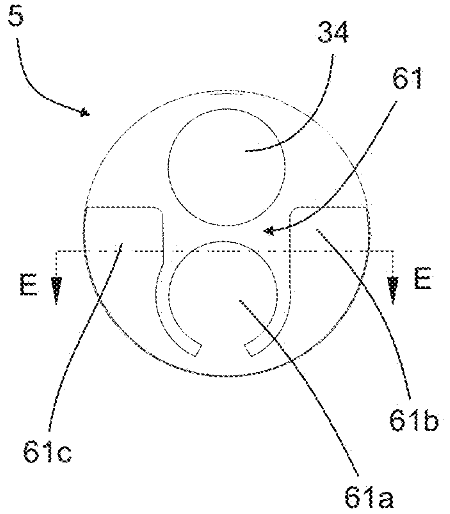
FIG. 4B shows a front view of the tip part of FIG. 4A with cross-sectional line E-E shown.
Figure 4C:
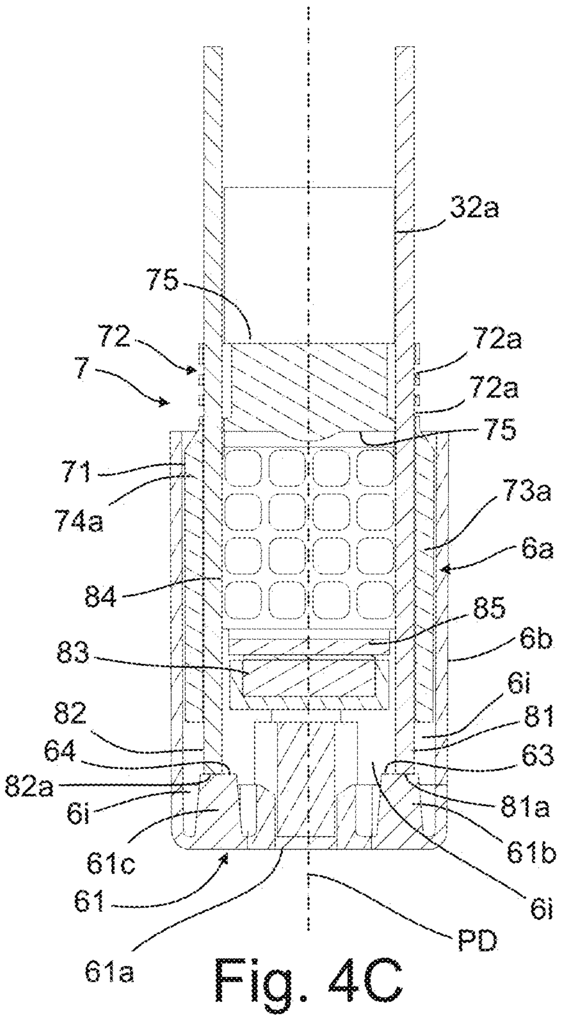
FIG. 4C shows a cross-sectional view of the tip part of FIG. 4B along the cross-section line E-E, in which the tip part is assembled.

As seen in FIGS. 2B and 3B, the exterior housing part 6 includes a proximal opening 6*d* and proximal rim surface 6*e*; a circumferentially extending side wall 6*a* with an exterior surface 6*b* and an interior surface 6*g* enclosing an interior space 6*h* configured for accommodating at least a proximal portion 8*a* of the camera assembly 8; and a distal end wall 61 with an image sensor window 61*a* and a first 61*b* and a second light guide 61*c* as seen in FIGS. 3A, 3B, and 4C. The distal end wall 61 forms the distal end 3*b* of the tip part 5.

As seen in FIG. 3C, the camera assembly 8 is positioned at a distal end 3*b* of the tip part 5 in the interior spacing 6*h* of the exterior housing part 6 so that an image sensor 83 is viewing out through a window 61*a* of the distal end wall 61 to allow an operator to inspect a distal body cavity when the insertion tube 3 is inserted into the body cavity. The camera assembly 61 comprises an image sensor 83 configured to capture an image, at least one lens with a light receival surface 83*a* configured to alter light received by the image sensor 83, a holder 85 for supporting the parts of the camera assembly 8, a first 81 and a second light source 82 configured to provide illumination for the image sensor 83, which in this embodiments is in the form of light emitting diodes, a printed circuit board 84, cables 87 (shown foreshortened in length for visualisation purposes) configured for carrying an image signal from the printed circuit board 84 to the monitor 11, and cables 87 configured for supplying power to the printed circuit board 84. The signal cables 87 and the power cables 87 are accommodated in a cable tube 32*a* (shown foreshortened in length for visualisation purposes) and are electrically connected to the printed circuit board 84. The printed circuit board 84 is configured to process a signal from the image sensor 83 and transmit the signal via signal cables 87 to the monitor cable 13 of the handle 2 for output to a monitor 11. The printed circuit board 84 includes a flexible folded connection 84*a*, 84*b* between each of the light sources 81, 82 and the image sensor 83 so that the light sources 81, 82 can be individually moved axially further from or closer to the image sensor 83.

As can be seen in FIGS. 3B and 3C, the tip part 5 further comprises an interior housing part 7 with a first tolerance compensating member 73, a second tolerance compensating member 74, a closure surface 71, and an attachment surface 72. The closure surface 71 extends circumferentially around a cavity 76 and coaxially and parallel with the proximal-distal axis PD so that, when the interior housing part 7 is positioned in the interior space 6*h*, a substantially uniform gap of about 20-50 micrometers is formed between closure surface 71 and the interior surface 6*g* as can be seen in FIG. 5B. The closure surface has an axial extent of about 1.1 mm. The interior housing part 7 further comprises a cable tube hole 75 forming a proximal access way into the cavity 76. The interior housing is prefabricated in one piece in an ultraviolet (UV) translucent or UV transparent material.

The first 73 and second tolerance compensating member 74 each has a distally positioned seat 73*b*, 74*b* configured for accommodating the respective light source 81, 82 and an arm 73*a*, 74*a* connecting said seat 73*b*, 74*b* with the closure surface 71. The interior housing part 7 narrows from the closure surface 71 to the attachment surface 72 which is positioned proximally in relation to the closure surface 71. The attachment surface 72 includes cut-outs 72*a* in the form of nine grooves for improving the mechanical connection to the distal end segment 41 of the bending section 4, but the number of grooves could in principle be more or less depending on specifics.

In another embodiment as shown in FIGS. 4A, 4B, and 4C, the first 81 and second light sources 82 are instead in the form of light fibres (shown foreshortened). Each light fibre has a distal end with a light emitting surface 81*a*, 82*a*, which in the post-compensation and assembled condition, abuts the respective second 63 and third stop surface 64 of the window 61*a*. The light fibres are typically not electrically connected to the printed circuit board 84 and the seat 73*b*, 74*b* of the tolerance compensating members 73, 74 can be omitted. Instead each light fibre 81, 82 extends along the respective arm 73*a*, 74*a* of the tolerance compensating member 73, 74 and are typically held and sealed by a mechanical connection, such as an adhesive connection, with the arm 73*a*, 74*a*, but a friction engagement could be applied additionally or alternatively to adhesive in order to maintain the position of each light fibre relative to the respective arm 73*a*, 74*a*.

The following describes the method of bringing the tip part 5 from a pre-compensation condition as shown in FIGS. 2B and 3B, onto a post-compensation condition as can be seen in FIGS. 3C and 4C, and further to an assembled condition as shown in FIGS. 2A and 5A-5C. Firstly, a camera assembly 8 is provided as described above, then cables 87 of the camera assembly 8 is inserted into the cable tube hole 75 from the distal direction to arrive at the arrangement shown in FIGS. 2B, 3B, and 4A. The camera assembly 8 is then guided into the interior housing part 7 so that a proximal portion of the holder 85 is positioned in the cavity 76, the first 81 and second light source 82 are positioned in and fixed to the respective first 73*b* and second seat 74*b* as shown in FIG. 3C, alternatively the light sources 81, 82 extend along and maintained in position by the mechanical connection with the arms 73*a*, 74*a* as shown in FIG. 4C. An upstanding guide portion 85*a* of the holder 85 centers the camera assembly 8 in the cavity 76. Simultaneously or alternatively afterwards, the cable tube 32*a* is positioned in the cable tube hole 75 wrapping around the cables 87 of the camera assembly 8. The interface 32*b* between the cable tube hole 75 and the cable tube 32*a*, as best seen in FIG. 5C, is then sealed by an adhesive.

Thirdly, an exterior housing part 6 is provided. The exterior housing part 6 comprises a circumferentially extending side wall 6*a* with a distal end wall 61 and a proximal rim surface 6*e* defining a proximal opening 6*d*. The circumferentially extending side wall 6*a* has an outer surface 6*b* and an interior surface 6*g*. The exterior housing part 6*a* defines an interior space 6*h* with a distal air volume 6*i*. The distal end wall 61 includes a window 61*a* with a first stop surface 62, a first light guide 61*b* with a second stop surface 63, and a second light guide 61*c* with a third stop surface 64. In this stage of the assembly method, the exterior housing part 6 could be interchanged with an assembly fixture instead.

Fourthly, the camera assembly 8 is then positioned so that the light receival surface 83*a* is in contact with the first stop surface 62. At this point, depending on dimensions and tolerances of the parts, either none, one, or both of the light emitting surfaces 81*a*, 82*a* of the light sources 81, 82 are in contact with their respective second 63 and third stop surface 64. To ensure that both the light sources 81, 82 are in contact with their respective stop surfaces 63, 64, the interior housing part 7 is urged in position by an operator pushing the attachment surface 72 distally so that the seats 73*b*, 74*b* of the tolerance compensating members 73, 74 or the mechanical connection between the arms 73*a*, 74*a* and the light sources 81, 82 pushes the respective light source 81, 82 in their respective optical axis 81*b*, 82*b* into contact with the respective stop surface 63, 64 thereby arriving at the post-compensation condition of the tip part 5 as can be seen in FIG. 3C or 4C.

Fifthly, either the interior housing part 7 is fixed to the exterior housing part 6 or, in the case of using the assembly fixture, the interior housing part 7 is fixed to the camera assembly 8, for instance to the holder 85.

Figure 5A:
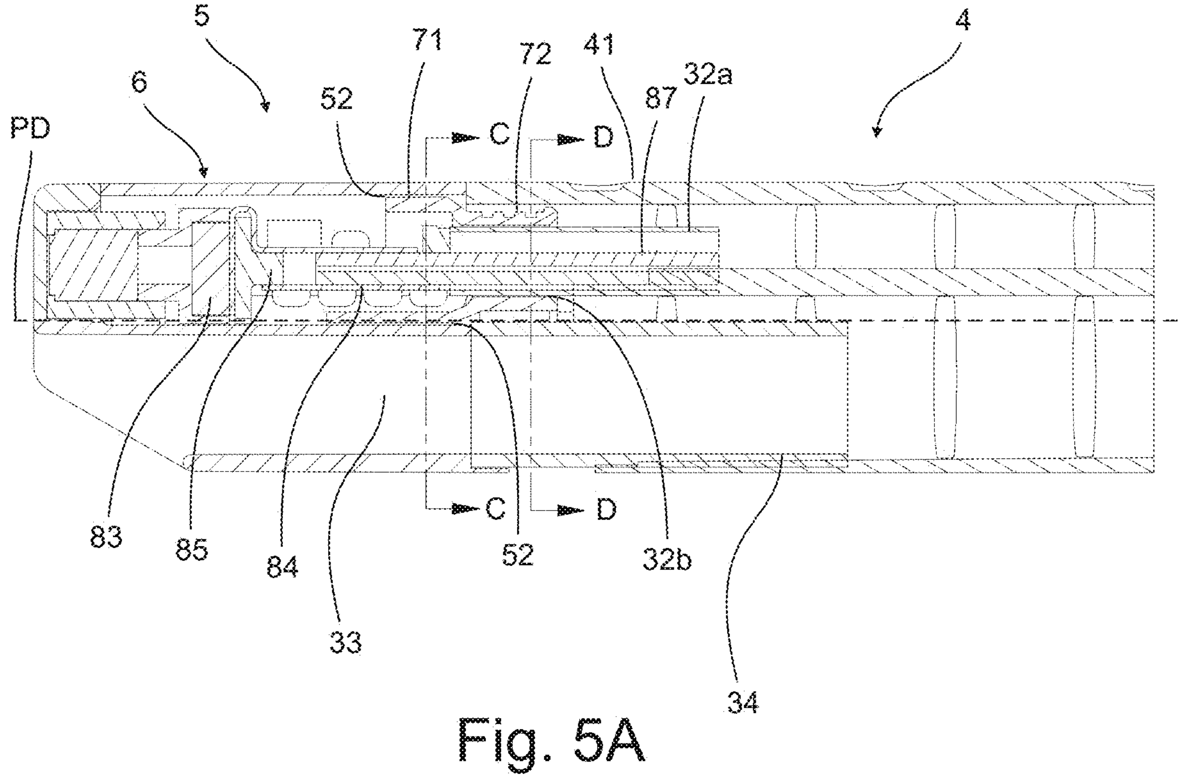
FIG. 5A shows a cross-sectional side view of the tip part of FIG. 3A along the cross-section line B-B.
Figure 5B:
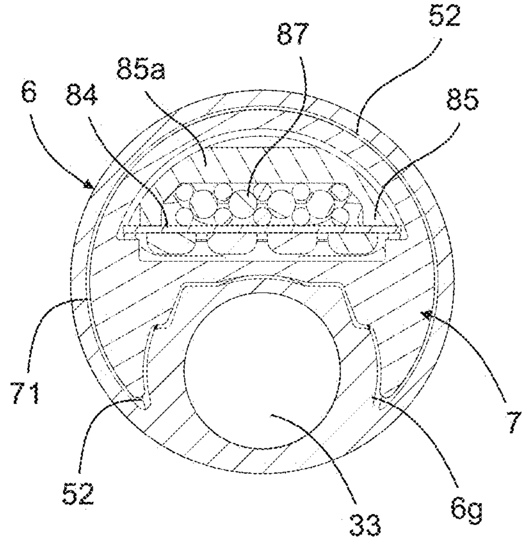
FIG. 5B shows a cross-sectional front view of the tip part of FIG. 5A along the cross-section line C-C.
Figure 5C:
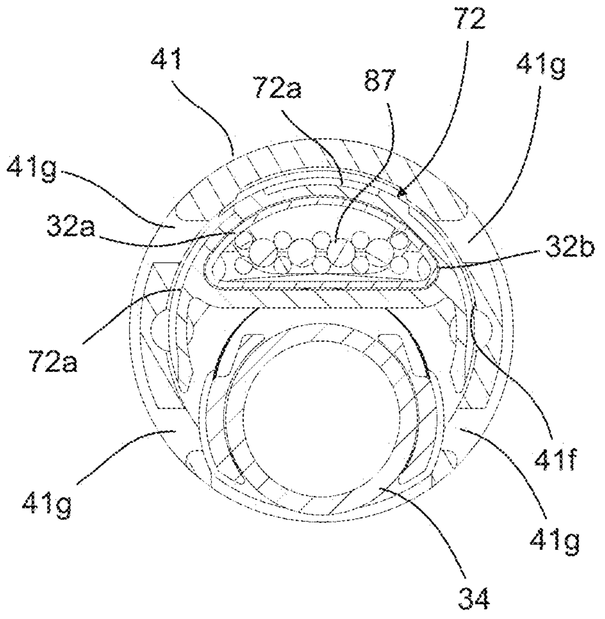
FIG. 5C shows a cross-sectional front view of the tip part of FIG. 5A along the cross-section line D-D.

The interior housing part 7 is fixed to the exterior housing part 6 by injecting an UV curable adhesive in the gap 52 between the closure surface 71 and the interior surface 6*g* of the exterior housing part 6 as best seen in FIGS. 5A and 5B (omitting the bending section 4 for now). A capillary effect then draws the adhesive into the gap 52 while ensuring that the adhesive does not flow out from distal end of the gap 52 and ensures that the adhesive is distributed around the circumference. Once the adhesive is sufficiently distributed, the adhesive is caused to harden by exposure to UV light which propagates through the UV translucent material of the interior housing part 7. In this case, the light sources are in the correct position with minimal air gap between the light emitting surfaces 81*a*, 82*a* and the respective stop surface 63, 64. Furthermore, the air volume around the light sources 81, 82 are liquid-sealed ensuring that the optical properties are not altered by ingressing liquids.

In the case of assembly using the assembly fixture, the interior housing part 7 is fixed to the holder 85 by injecting adhesive in a gap between the guide portion 85*a* of the holder 85 and an interior surface of the interior housing part 7 opposite the closure surface 71, and thereafter causing the adhesive to harden by exposure to UV light. The combined interior housing 7 and camera assembly 8 can then be fitted into an exterior housing by the above method. In this case, any air gap between the light emitting surfaces 81*a*, 82*a* and the respective stop surface 63, 64 depends on the tolerances of the injection moulded exterior housing part 6 and the assembly fixture which can be manufactured with relatively tight tolerances.

Sixthly, as can be seen in FIG. 5C, the distal end segment 41 of the bending section 4 is positioned adjacent to and overlapping with the attachment surface 72 of the interior housing part 7. Adhesive is then injected through holes 41*g* so that the adhesive fills said holes 41*g* and the grooves 72*a* of the attachment surface 72 and further wets the interior surface 41*f* of the distal end segment 41 to fix the interior housing part 7, and thereby the exterior housing part 6 and camera assembly 8, to the bending section 4 to arrive at the assembled condition of the tip part 5.

ADDITIONAL EMBODIMENTS

1. A tip part for an endoscope, the tip part having a pre-compensation condition and a post-compensation condition, and comprising: a camera assembly having an image sensor and a first light source configured for emitting light along an optical axis thereof to provide illumination of an object to be visualized by the image sensor; and a first tolerance compensating member being configured to, in the pre-compensation condition, allow adjustment of the distance between the first light source and the image sensor along the optical axis of the first light source and being configured to, in the post-compensation condition, maintain the distance be-tween the first light source and the image sensor at least along the optical axis of the first light source.

2. A tip part according to embodiment 1, wherein the first tolerance compensating member is configured to, in the pre-compensation condition, move the first light source along the optical axis of the first light source relative to the image sensor.

3. A tip part according to any one of the previous embodiments, wherein the first tolerance compensating member comprises a seat configured for guiding the adjustment of the distance between the first light source and the image sensor along the optical axis of the first light source.

4. A tip part according to any one of the previous embodiments, wherein the optical axis is a longitudinal optical axis.

5. A tip part according to any one of the previous embodiments, wherein the first light source is fixed to the first tolerance compensating member, potentially by an adhesive.

6. A tip part according to any one of the previous embodiments, wherein the tip part further comprises a printed circuit board being electrically connected to both the image sensor and the first light source.

7. A tip part according to any of the previous embodiments, comprising: an exterior housing part including a circumferentially extending side wall with a proximal opening, the circumferentially extending side wall defining an interior space with an air volume; and an interior housing part including a circumferentially extending closure surface and the first tolerance compensating member, the interior housing part being positioned in the proximal opening of the exterior housing part, the tolerance compensating member and the interior housing part being integrally formed in one piece; wherein the camera assembly includes a distal portion and is positioned in the interior space so that the air volume envelops at least the distal portion of the camera assembly, and wherein the exterior housing part and interior housing part are formed as separate prefabricated components, and wherein the closure surface, in the post-compensation condition, closes the proximal opening of the exterior housing so as to liquid-seal the air volume in tip part and fix the first light source relative to the image sensor.

8. A tip part according to embodiment 7, wherein the interior housing part comprises a circumferentially extending attachment surface, wherein, when the interior housing part is positioned in the proximal opening of the exterior housing part, the attachment surface extends proximally from the proximal opening and is configured for attaching the interior housing part to another element of the tip part.

9. A tip part according to embodiment 8, wherein the attachment surface comprises one or more cut-outs configured for accommodating hardened adhesive to improve the mechanical connection between the attachment surface and the other element of the tip part.

10. A tip part according to any one of embodiments 8 to 9, further comprising a bending section including a number of hingedly interconnected segments including a distal end segment, a proximal end segment, and a plurality of intermediate segments positioned between the proximal end segment and the distal end segment, wherein the attachment surface of the interior housing part is attached to the distal end segment.

11. A tip part according to any one of embodiments 7 to 10, wherein a gap is formed between the closure surface and an interior surface of the exterior housing part in the pre-compensation condition and when the interior housing part is positioned in the proximal opening of the exterior housing part, the gap being filled with a hardened adhesive in the post-compensation condition so as to liquid-seal the air volume and fix the first light source relative to the image sensor.

12. A tip part according to any one of embodiments 7 to 11, wherein the interior housing part comprises a cavity configured for accommodating and aligning a guide portion of the camera assembly at the proximal end thereof.

13. A tip part according to any one of embodiments 7 to 12, wherein the interior housing part comprises a hole configured for allowing a cable tube accommodating a plurality of cables electrically connected to the camera assembly to be inserted there through.

14. An endoscope comprising a tip part according to any one of the previous embodiments.

15. A system for visually inspecting inaccessible places such as human body cavities, the system comprising: an endoscope according to embodiment 14 and a monitor, wherein the endoscope is connectable to the monitor, and the monitor allows an operator to view an image captured by the camera assembly of the endoscope.

16. A method for preparing a tip part for an endoscope, comprising the steps of: providing a tip part according to any one of embodiments 1 to 13; positioning a surface of the camera assembly in contact with a camera stop surface of another part; adjusting the first tolerance compensating member so that the first light source is moved in contact with a second stop surface of the other part along the optical axis of the first light source; and fixing the first light source in relation to the image sensor.

LIST OF REFERENCES

The following is a list of reference numerals used throughout this disclosure. In case of any doubt, the reference numerals of the following list apply.

1 endoscope
11 monitor
12 cable socket
13 monitor cable
2 handle
21 control lever
3 insertion tube
3*a* proximal end
3*b* distal end
32*a* cable tube
32*b* interface
33 working passage
34 working tube
4 bending section
41 distal end segment
41*a* distal end
41*f* interior surface
41*g* hole
42 intermediate segment
43 proximal end segment
44 hinge member
5 tip part
52 gap
6 exterior housing part
6*a* circumferentially extending side wall
6*b* outer surface
6*d* proximal opening
6*e* proximal rim surface
6*g* interior surface
6*h* interior space
6*i* air volume
61 distal end wall
61*a* window
61*b* first light guide
61*c* second light guide
62 first stop surface
63 second stop surface
64 third stop surface
7 interior housing part
71 closure surface
72 attachment surface
72*a* groove
73 first tolerance compensating member
73*a* arm
73*b* seat
74 second tolerance compensating member
74*a* arm
74*b* seat
75 cable tube hole
76 cavity
8 camera assembly
81 first light source
81*a* first light emitting surface
81*b* optical axis
82 second light source
82*a* second light emitting surface
82*b* optical axis
83 image sensor
83*a* light receival surface
84 printed circuit board
84*a* folded connection
84*b* folded connection
85 holder
85*a* guiding portion
86 lens barrel
87 cable
9 flexible tube
PD proximal-distal axis

We claim:

1. A method for assembling an endoscope, the method comprising:

providing a handle attached to an insertion cord, the insertion cord including at least an insertion tube and a bending section;

inserting at least a portion of a camera assembly into an exterior housing through a proximal opening of the exterior housing, the camera assembly comprising an image sensor, and the exterior housing comprising a camera window, a light source window, a camera stop surface and a light source stop surface;

inserting at least a portion of an interior housing into the exterior housing through the proximal opening of the exterior housing, the interior housing comprising a wall, an arm and a seat surface, the wall including a closure surface, the arm connected to and extending distally from the wall, and the seat surface connected to the arm, the interior housing being configured to translate independently of the image sensor;

translating the camera assembly distally until the camera assembly contacts the camera stop surface, the camera stop surface preventing further distal translation of the camera assembly;

translating the interior housing distally, independently of the image sensor, to translate a light emitting diode (LED) to a post-compensation condition in which the LED is positioned between the seat surface and the light source stop surface without an air gap therebetween, the light source stop surface being traversed by an optical axis of the LED and preventing further distal translation of the LED, wherein translating the interior housing distally adjusts an axial distance between the image sensor and the LED; and while the camera assembly contacts the camera stop surface and the LED is in the post-compensation condition, adhesively bonding the interior housing to an interior surface of the exterior housing.

2. The method of claim 1, further comprising connecting a flexible circuit board to the LED and the camera assembly, the flexible circuit board permitting independent movement of the LED relative to the image sensor, wherein inserting the at least the portion of the camera assembly into the exterior housing positions the LED distally of the seat surface prior to the insertion of the interior housing into the exterior housing, and wherein translating the interior housing distally is performed while the camera assembly contacts the camera stop surface.

3. The method of claim 1, further comprising connecting a flexible circuit board to the LED and the camera assembly, the flexible circuit board permitting independent movement of the LED relative to the image sensor, wherein translating the interior housing distally is performed while the camera assembly contacts the camera stop surface.

4. The method of claim 1, further comprising connecting a flexible circuit board to the LED and the camera assembly, the flexible circuit board permitting independent movement of the LED relative to the image sensor, mounting the flexible circuit board and the camera assembly onto a camera assembly holder comprising a guide portion, and adhesively bonding the guide portion to an interior surface of the wall of the interior housing, the interior surface being opposite the closure surface, wherein translating the interior housing distally is performed while the camera assembly contacts the camera stop surface.

5. The method of claim 1, wherein translating the interior housing distally is performed while the camera assembly contacts the camera stop surface.

6. The method of claim 1, further comprising connecting a flexible circuit board to the LED and the camera assembly, the flexible circuit board permitting independent movement of the LED relative to the image sensor.

7. The method of claim 1, wherein the interior housing comprises an attachment surface proximal of the closure surface, the method further comprising adhesively bonding the attachment surface to the bending section, wherein adhesively bonding the interior housing to the interior surface of the exterior housing closes the proximal opening of the exterior housing to liquid-seal an interior space of the exterior housing.

8. The method of claim 1, wherein the interior housing comprises an attachment surface proximal of the closure surface, the method further comprising adhesively bonding the attachment surface to the bending section after adhesively bonding the interior housing to the interior surface of the exterior housing.

9. The method of claim 1, further comprising molding in one-piece the exterior housing, wherein the camera window and the light source window are molded from a transparent polymer, wherein the exterior housing comprises a circumferential wall and opaque portions of a front wall, the opaque portions of the front wall molded of an opaque material, and wherein the opaque portions of the front wall surround and are fused to the camera window and the light source window.

10. The method of claim 1, further comprising molding in one-piece segments and hinges, the hinges connecting the segments to each other to form the bending section.

11. The method of claim 1, further comprising connecting a flexible circuit board to the LED and the camera assembly, mounting the flexible circuit board and the camera assembly onto a camera assembly holder comprising a guide portion, adhesively bonding the guide portion to an interior surface of the wall of the interior housing, the interior surface being opposite the closure surface, filling with adhesive a gap formed between the closure surface and the interior surface of the exterior housing, and curing the adhesive to liquid-seal the gap.

12. The method of claim 11, wherein a tip part comprises the camera assembly, the exterior housing, and the interior housing, the method further comprising: after curing the adhesive, testing the tip part for liquid tightness, and if the testing verifies liquid tightness, attaching the tip part to the bending section.

13. The method of claim 1, further comprising filling with adhesive a gap formed between the closure surface and the interior surface of the exterior housing and curing the adhesive to liquid-seal the gap.

14. The method of claim 13, wherein a tip part comprises the camera assembly, the exterior housing, and the interior housing, the method further comprising: after curing the adhesive, testing the tip part for liquid tightness, and if the testing verifies liquid tightness, attaching the tip part to the bending section.

15. The method of claim 1, further comprising aligning a cavity of the interior housing with a guide portion of the camera assembly, the cavity and the guide portion configured to guide translation of the camera assembly relative to the interior housing.

16. The method of claim 1, further comprising molding in one-piece the exterior housing, wherein the camera window, light guides, and the light source window are molded from a transparent polymer, the light guides being connected to and extending proximally from the light source window, wherein the exterior housing comprises a circumferential wall and opaque portions of a front wall, the opaque portions of the front wall molded of an opaque material, wherein the opaque portions of the front wall surround and are fused to the camera window and the light source window, wherein the LED is positioned between the seat surface and one of the light guides without an air gap therebetween.

17. The method of claim 16, wherein the interior housing further comprises a second arm and a second seat surface, the second arm connected to and extending distally from the wall in parallel with the arm, and wherein the second seat surface is connected to the second arm, the method further comprising connecting a flexible circuit board to a second LED, the flexible circuit board permitting independent movement of the second LED relative to the image sensor, wherein the second LED is positioned between the second seat surface and a second one of the light guides without an air gap therebetween.

* * * * *